US012564599B2

(12) United States Patent
Glas

(10) Patent No.: US 12,564,599 B2
(45) **Date of Patent: *Mar. 3, 2026**

(54) PHARMACEUTICAL COMPOSITION COMPRISING TETRAHYDROCANNABIVARIN FOR THE PREVENTION AND TREATMENT OF OVERWEIGHT

(71) Applicants: CepVentures International Corporation, Anguilla (AI); LIV INNOVATION SA, Lugano (CH)

(72) Inventor: Ronald Johannes Glas, Lugano (CH)

(73) Assignees: CepVentures International Corporation, Anguilla (AI); LIV INNOVATION SA, Lugano (CH)

( * ) Notice: Subject to any disclaimer, the term of this patent is extended or adjusted under 35 U.S.C. 154(b) by 1055 days.

This patent is subject to a terminal disclaimer.

(21) Appl. No.: 17/432,851

(22) PCT Filed: Feb. 21, 2020

(86) PCT No.: PCT/NL2020/050110

§ 371 (c)(1),
(2) Date: Aug. 20, 2021

(87) PCT Pub. No.: WO2020/171711

PCT Pub. Date: Aug. 27, 2020

(65) Prior Publication Data

US 2022/0168265 A1 Jun. 2, 2022

(30) Foreign Application Priority Data

Feb. 21, 2019 (NL) ..................................... 2022615

(51) Int. Cl.
*A61K 31/00* (2006.01)
*A61P 3/04* (2006.01)

(52) U.S. Cl.
CPC .............. *A61K 31/658* (2023.05); *A61P 3/04* (2018.01)

(58) Field of Classification Search
CPC .... A61K 31/352; A61K 31/05; A61K 31/658; A61P 3/04
See application file for complete search history.

(56) References Cited

FOREIGN PATENT DOCUMENTS

| | | | | |
|---|---|---|---|---|
| CA | 3045841 | 10/2019 | | |
| GB | 2434097 | 7/2007 | | |
| WO | 2006/054057 | 5/2006 | | |
| WO | WO 2017/137992 | 8/2017 | | |
| WO | WO-2018023166 A1 * | 2/2018 | | A61K 31/01 |
| WO | WO-2019241804 A1 * | 12/2019 | | A61K 31/05 |

OTHER PUBLICATIONS

ElSohly, Mahmoud A., and Desmond Slade. "Chemical Constituents of Marijuana: The Complex Mixture of Natural Cannabinoids." Life Sciences, vol. 78, No. 5, Dec. 2005, pp. 539-548. ScienceDirect, https://doi.org/10.1016/j.lfs.2005.09.011. (Year: 2005).*

U.S. Appl. No. 62/685,903, filed Jun. 15, 2018. Priority document for WO-2019241804-A1. (Year: 2018).*

O'Shaughnessy ("THCV plants being grown for medical use in California; Cannabinoid may counter metabolic-syndrome symptoms", O'Shaughnessy's Winter 2015/16. https://beyondthc.com/1-the-9-solution/. Accessed Jan. 29, 2025). (Year: 2015).*

International Search Report, International Patent Application No. PCT/NL2020/050110, mailed May 29, 2020, 4 pages.

Gernot Riedel et al. "Synthetic and plant-derived cannabinoid receptor antagonists show hypophagic properties in fasted and non-fasted mice: Cannabinoid antagonists as anorectic agents" British Journal of Pharmacology, vol. 156, No. 7, Mar. 31, 2009, pp. 1154-1166.

Brierley, D. et al. "Cannabigerol is a novel, well-tolerated appetite stimulant in pre-satiated rats" Psychopharmacology 2016, 233: 3603-3613.

Farrimond, J. et al. "Cannabinol and cannabidiol exert opposing effects on rat feeding patterns" Psychopharmacology 2012, 223: 117-129.

Tudge, L. et al. "Neural Effects of Cannabinoid CB1 Neutral Antagonist Tetrahydrocannabivarin on Food Reward and Aversion in Healthy Volunteers" International Journal of Neuropsychopharmacology, 2015, 1-9.

Russo EB, "Taming THC: potential cannabis synergy and phytocannabinoid-terpenoid entourage effects", Br J Pharmacol. Aug. 2011;163(7):1344-64. doi: 10.1111/j.1476-5381.2011.01238.x. PMID: 21749363; PMCID: PMC3165946.

* cited by examiner

*Primary Examiner* — Clinton A Brooks
*Assistant Examiner* — Kyle Nottingham
(74) *Attorney, Agent, or Firm* — Casimir Jones, S.C.; Robert A. Goetz

(57) ABSTRACT

The present invention relates to a pharmaceutical composition comprising a tetrahydrocannabivarin (THCV), wherein the composition further comprises cannabigerol (CBG) or cannabinodiol (CBND) or a mixture thereof, for use in the prevention and treatment of overweight, preferably associated with obesitas. The pharmaceutical composition according to the invention may further comprise the following additional compounds tetrahydrocannabinol (THC), or Cannabigerol (CBG) or Cannabinodiol (CBND) or a combination thereof.

9 Claims, 1 Drawing Sheet

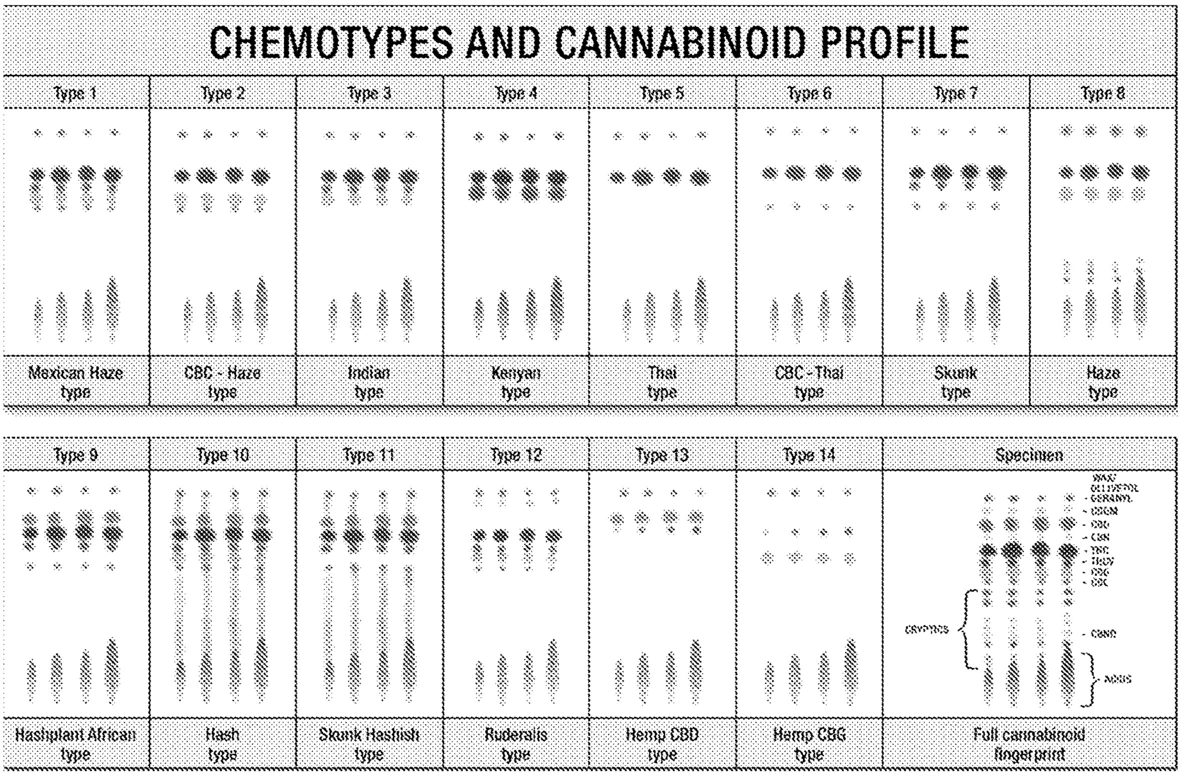
CHEMOTYPES AND CANNABINOID PROFILE
Type 1
Type 2
Type 3
Type 4
Type 5
Type 6
Type 7
Type 8
Mexican Haze type
CBC - Haze type
Indian type
Kenyan type
Thai type
CBC - Thai type
Skunk type
Haze type
Type 9
Type 10
Type 11
Type 12
Type 13
Type 14
Specimen
WAX
OLIVETOL
GERANYL
CBN
THC
THCV
Hashplant African type
Hash type
Skunk Hashish type
Ruderalis type
Hemp CBD type
Hemp CBG type
Full cannabinoid fingerprint

PHARMACEUTICAL COMPOSITION COMPRISING TETRAHYDROCANNABIVARIN FOR THE PREVENTION AND TREATMENT OF OVERWEIGHT

FIELD OF THE INVENTION

The present invention relates to a pharmaceutical composition comprising a tetrahydrocannabivarin (THCV), wherein the composition further comprises cannabigerol (CBG) or cannabinodiol (CBND) or a mixture thereof, for the prevention and treatment of overweight including obesity and related disorders. The present invention also relates to a method for treating a mammal suffering from overweight or a related disorder, wherein a pharmaceutical composition comprising a tetrahydrocannabivarin is administered to said mammal.

BACKGROUND OF THE INVENTION

Obesity, which can be defined as a body weight more than 20% above the ideal body weight or even better by a Body Mass Index (BMI; expressed as the ratio of the mammal's weight and the square of its length) of 30 $kg/m^2$ or higher (cf. World Health Organization. Technical report series 894: "Obesity: preventing and managing the global epidemic.", Geneva, World Health Organization, 2000), is a rapidly increasing global problem that urgently needs to be controlled. Obesity is the result of a positive energy balance, as a consequence of increased ratio of caloric intake to energy expenditure. The molecular factors regulating food intake and body weight balance are incompletely understood. (B. Staels et al., J. Biol. Chem. 270(27), 15958, 1995; F. Lonnquist et al., Nature Medicine 1(9), 950, 1995). Although the genetic and/or environmental factors leading to obesity are poorly understood, several genetic factors have been identified.

Obesity causes or exacerbates many health problems, both independently and in association with other disorders. The medical problems associated with obesity, which can be serious and life-threatening, include hypertension, type 2 diabetes mellitus, elevated plasma insulin concentrations; insulin resistance, dyslipidemias, hyperlipidemia, endometrial, breast-, prostate- and colon-cancer, osteoarthritis, respiratory complications, cholelithiasis, gallstones, arteriosclerosis, heart disorder, abnormal heart rhythms, and heart arrythmias. Reference is for example made to US 2006/276549 and WO 2006/124506 to Abbot Laboratories.

Nowadays, three medical compounds are used for the treatment of obesity, i.e. Rimonabant (Acomplia®; a CB1 cannabinoid receptor antagonist), Sibutramine (Meridia®; a neurotransmitter reuptake inhibitor) and Orlistat (Xenical®; a pancreatic lipase inhibitor). Reference is made to U.S. Pat. Nos. 6,538,034 and 4,598,089, incorporated by reference, and to the scientific articles Despres et al., "Effects of Rimonanbant on metabolic risk factors in overweight patients with dyslipidemia", N. Eng. J. Med, 353, 2121-2134, 2005, Despres et al., "Effects of Rimonibant on metabolic risk factors in overweight patients with dyslipidemia", N. Eng. J. Med. 353, 2121-2134, 2005; and Li et al., "Pharmacologic treatment of obesity", Ann. Intern. Med. 142, 532-546, 2005, all incorporated by reference. Although weight reductions of this magnitude do produce some favourable metabolic effects, the improvements are modest and are insufficient in treating more obese mammals.

Combinations of the pharmaceutically active agents Rimonabant, Sibutramine or Orlistat with other active components are disclosed in U.S. Pat. Nos. 7,037,944, 7,148,258, US 2005/124660, US 2006/135471, US 2006/269510, US 2006/276549, US2007/060532 and US 2007/142369, incorporated by reference. However, the combinations do not seem to a significantly greater weight reduction compared to single-drug treatment (cf. Padwal, R. S. and Majumdar, S. R., The Lancet 369, 71-77, 2007, incorporated by reference).

Studies of the weight loss medications Orlistat (Davidson, M. H. et al., JAMA 281, 235-42, 1999), Dexfenfluramine (Guy Grand, B. et al., Lancet 2, 1142-5, 1989), Sibutramine (Bray, G. A. et al. Obes. Res., 189-98, 1999) and Phentermine (Douglas, A. et al., Int. J. Obes. 7, 591-5, 1983) have demonstrated a weight loss of about 5%-10% of body weight for drug compared to placebo. In particular, Sibutramine reduces body weight by about 10% over a 6 month or a 1 year period. Studies have also found that Sibutramine potently inhibits food intake and decreases body weight initially. Studies have shown that Sibutramine reduces body weight by a dual mode of action; it decreases food intake by enhancing satiety (Fantino, M. & Souquet, A.-M., Int. J. Obesity, 19, 145, 1995; Halford, J. C. G., Heal, D. J. & Blundell, J. E., Brit. J. Pharmacol. 114, 387P, 1995; and Stricker-Krongrad, A., Souquet, A.-M. & Burlet, C. Int. J. Obesity, 19, 145, 1995), and it increases energy expenditure by stimulating thermogenesis (Connoley, I. P., Heal, D. J. & Stock, M. J., Brit. J. Pharmacol. 114, 388P, 1995; and Connoley, I. P., Frost, I., Heal, D. J. & Stock, M. J., Brit. J. Pharmacol. 117, 170P, 1996).

However medicaments such as Sibutramine and Rimonabant show adverse side-effects, e.g. dry mouth, paradoxically increased appetite, nausea, strange taste in the mouth, anorgasmia and delayed ejaculation, upset stomach, constipation, trouble sleeping, dizziness, drowsiness, menstrual cramps/pain, headache, flushing, or joint/muscle pain. Sibutramine can substantially increase blood pressure and pulse in some patients and "suicide" records are recently reported for Rimonabant. None of the currently used treatments for obesity is capable of fully relieving the symptoms in all cases. Patients frequently combine different treatments in an attempt to address all of their symptoms. Clearly, although numerous treatments have been developed in an attempt to control obesity there is still a need in the art for effective treatments. According to the first and second aspect of the present invention, is to provide such a fundamental new way of treating obesity in a natural (biological) non synthetic manner.

Cannabinoids are organic compounds that are exclusively found in *Cannabis sativa, ruderalis*, indica strains and their blends. *Cannabis sativa* is the natural source of a set of at least 66 oxygen-containing aromatic hydrocarbon compounds that are known collectively as phytocannabinoids (ElSohly, M. A., "Chemical constituents of *Cannabis*, In: Grotenhermen, F. and Russo, E., editors. *Cannabis* and cannabinoids: Pharmacology, Toxicology and Therapeutic Potential". Binghamton (NY): Haworth Press, 2002: 27-36). The n-propyl analogue of Δ-9 tetrahydrocannabinol (THC) which was first detected in *cannabis* by Gill et al. (Gill, E. W., Paton, W. D. M., Pertweee, R. G., "Preliminary Experiments on the chemistry and pharmacology of *cannabis*", Nature 228, 134-136, 1970) and named Δ-9 tetrahydrocannabivarin (THCV) by Merkus (Merkus, F. W. H. M., "Cannabivarin and tetrahydrocannabivarin, two new constituents of hashish", Nature 232, 579-580, 1971).

GB 2377633 A of GW Pharma Ltd. discloses pharmaceutical compositions comprising cannabinoids having specific ratios of cannabidiol (CBD) to tetrahydrocannabinol (THC), wherein the CBD is present in an amount greater than the amount of THC. The compositions are clinically useful in the treatment or management of specific diseases or medical conditions including inflammatory diseases, diseases or conditions wherein oxidative stress plays a role, psychotic disorders, epilepsy, movement disorders, stroke, head injuries, diseases which require appetite suppression, multiple sclerosis, spinal cord injury, peripheral neuropathy, cancer pain and migraine. The pharmaceutical compositions may further comprise THCV (tetrahydrocannabinovarin) and CBDV (cannabidivarin). However, Table 1 of GB 2377633 A attributes the appetite suppressing activity solely to CBD.

GB 2414933 A of GW Pharma Ltd. discloses the use of a combination of cannabinoids for the treatment of pain, inflammation and/or disease modification in arthritis. The cannabinoids are selected from CBD or cannabidivarin (CBDV) and THC or tetrahydrocannabinovarin (THCV) and are in a predefined ratio by weight of less than or equal to 19:1 of CBD or CBDV to THC or THCV.

In addition, not every patient suffering from overweight is in need of a synthetic medicament or has objections against such products. There is therefore a need in the art for natural products which can be used for treating overweight and related disorders such as obesity.

DESCRIPTION OF THE DRAWINGS

FIG. 1 shows the chemotypes and their cannabinoid profiles.

SUMMARY OF THE INVENTION

The present invention relates to a pharmaceutical composition comprising a tetrahydrocannabivarin (THCV), wherein the composition further comprises cannabigerol (CBG) or cannabinodiol (CBND) or a mixture thereof, for use in the prevention and/or treatment of overweight. The present invention further relates to a method for treating a mammal suffering from overweight or a related disorder, wherein a pharmaceutical composition comprising a tetrahydrocannabivarin (THCV), wherein the composition further comprises cannabigerol (CBG) or cannabinodiol (CBND) or a mixture thereof, is administered to said mammal in a therapeutically effective, non-toxic amount to induce weight loss.

The present invention relates to a pharmaceutical composition comprising a tetrahydrocannabivarin (THCV), wherein the composition further comprises cannabigerol (CBG) or cannabinodiol (CBND) or a mixture thereof, for the prevention and treatment of overweight. The present invention further relates to a method for treating a mammal suffering from overweight or a related disorder, wherein a pharmaceutical composition comprising a tetrahydrocannabivarin (THCV), wherein the composition further comprises cannabigerol (CBG) or cannabinodiol (CBND) or a mixture thereof, is administered to said mammal.

DETAILED DESCRIPTION OF THE INVENTION

The verb “to comprise” as is used in this description and in the claims and its conjugations are used in its non-limiting sense to mean that items following the word are included, but items not specifically mentioned are not excluded. In addition, reference to an element by the indefinite article “a” or “an” does not exclude the possibility that more than one of the element are present, unless the context clearly requires that there is one and only one of the elements. The indefinite article “a” or “an” thus usually means “at least one”.

In this document, the term “tetrahydrocannabivarin” is abbreviated as THCV. However, this term encompasses the group of compounds consisting of Δ9-tetrahydrocannabivarin, Δ8-Tetrahydrocannabivarin, and mixtures thereof. The compound Δ9-tetrahydrocannabivarin is also known as 6,6,9-trimethyl-3-propyl-5" 6a,7,8,10a-tetrahydrobenzo[c] chromen-1-ol (CAS. No. 28172-17-0). In an embodiment of the present invention, tetrahydrocannabivarin (THCV) is selected from the group consisting of Δ9-tetrahydrocannabivarin (THCV), Δ8-tetrahydrocannabivarin (Δ8-THCV), and one or more mixtures thereof.

The compound Δ9-tetrahydrocannabivarin is a psychoactive cannabinoid and is found in the hemp plant *Cannabis sativa.* It is an analogue of THC wherein the side chain is shortened by two CH2 groups. The compound Δ9-tetrahydrocannabivarin can be used as a marker compound to differentiate between the consumption of hemp 10" products and synthetic THC. The compound Δ9-tetrahydrocannabivarin THCV is found in largest quantities from Indica strains.

Tetrahydrocannabinol (THC) is also known as (−)-(6aR, 10aR)-6,6,9-trimethyl-3-pentyl-6a,7,8,10a-tetrahydro-6H-benzo[c]chromen-1-ol (CAS. No. 1972-08-3). In this document, the term THC also includes 9'- or 8'-carboxylated analogs (e.g. carboxylic acids and carboxylic acid esters) thereof, e.g. 11-nor-9-carboxy-Δ9-tetrahydrocannabinol (1-hydroxy-6,6-dimethyl-3-pentyl-6a,7,8,10a-tetrahydrobenzo[c]-chromene-9-carboxylic acid; Cas. No. 64280-14-4).

Cannabigerol (CBG) is also known as (E)-2-(3,7-Dimethylocta-2,6-dienyl)-5-pentylbenzene-1,3-dial (CAS. Nos. [2808-33-5], [25654-31-3] (E); [9500-1-70-0] undefined configuration. Isomers: [25654-32-4] (Z)). CBG-analogues according to Formula 1 are listed in Table 1.

Formula 1

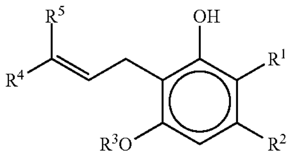

TABLE 1

| CBG-analogues according to Formula 1 | | | | | | |
|---|---|---|---|---|---|---|
| Compound | Cis/Trans | $R^1$ | $R^2$ | $R^3$ | $R^4$ | $R^5$ |
| Cannabigerolic acid A [(E)-CBGA-$C_5$ A] | cis | COOH | n-$C_5H_{11}$ | H | $(CH_2)_2CH{=}C(CH_3)_2$ | OH |

TABLE 1-continued

CBG-analogues according to Formula 1

| Compound | Cis/Trans | $R^1$ | $R^2$ | $R^3$ | $R^4$ | $R^5$ |
|---|---|---|---|---|---|---|
| Cannabigerolic acid A monomethyl ether [(E)-CBGAM-$C_5$ A] | cis | COOH | n-$C_5H_{11}$ | Me | $(CH_2)_2CH{=}C(CH_3)_2$ | Me |
| Cannabigerol [(E)-CBG-$C_5$] | cis | H | n-$C_5H_{11}$ | H | $(CH_2)_2CH{=}C(CH_3)_2$ | OH |
| Cannabigerol monomethyl ether [(E)-CBGM-$C_5$] | cis | H | n-$C_5H_{11}$ | Me | $(CH_2)_2CH{=}C(CH_3)_2$ | Me |
| Cannabigerovarinic acid A [(E)-CBGVA-$C_3$ A] | cis | COOH | n-$C_3H_7$ | H | $(CH_2)_2CH{=}C(CH_3)_2$ | OH |
| Cannabigerovarin [(E)-CBGV-$C_3$] | cis | H | n-$C_3H_7$ | H | $(CH_2)_2CH{=}C(CH_3)_2$ | OH |
| Cannabinerolic acid A [(Z)-CBGA-$C_5$ A] | trans | COOH | n-$C_5H_{11}$ | H | Me | $(CH_2)_2CH{=}C(CH_3)_2$ |

Cannabinodiol (CBND) is also known as 2-((1S,6S)-3-methyl-6-(prop-1-en-2-yl) cyclohex-2-enyl)-5-pentylbenzene-1,3-diol (CAS. No. 13956-29-1). CBND analogues are shown in Formula 2.

Formula 2

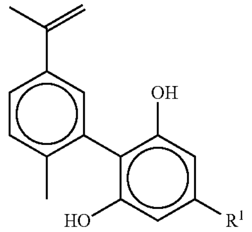

R1 = $CH_3$, $C_2H_5$, $C_3H_7$ or $C_4H_9$

As will be apparent to the person skilled in the art, one or more of THCV, THC, CBG and CBND may be synthetic. However, it is preferred that they are obtained from natural sources.

Instead of CBG, analogues may be used wherein these analogues are selected from the compounds shown above in Formula 1 and Table 1. Instead of CBND, analogues may be used wherein these analogues are selected from the compounds shown above in Formula 2.

In this document, the term "overweight" encompasses obesity and related disorders and metabolic syndrome related disorders. In an embodiment of the present invention, the use in the prevention and treatment of overweight is the use in the prevention and treatment of overweight associated with obesity.

According to the invention, it is preferred that the pharmaceutical composition comprises sole THCV and CBND and CBG oil. According to the invention, it is preferred that the pharmaceutical composition (of *Cannabis simplex*), due to synergistic effects between THCV and THC, further comprises THC. It was found that the ratio by weight of THCV and THC (THCV:THC) is important in which degree weight loss is induced/appetite is reduced. In an embodiment, the ratio of THCV:THC by weight is between about 10:1 and about 1:10. In a preferred embodiment, the ratio of THCV:THC by weight is between about 1:5 and about 5:1. In another preferred embodiment, the ratio of THCV:THC by weight is between about 1:1 and about 10:1.

A high THCV content has a beneficial effect on weight loss. It is therefore preferred that the pharmaceutical composition comprises a TCHV and THC, wherein the ratio of the THCV:THC by weight is between about 10-1, more preferably about 5:1, even more preferably about 1:1. However, in all these ranges, it is preferred that the TCHV content is higher than the THC content to avoid (unwanted) psychotropic side effects.

According to the invention, the pharmaceutical composition may comprises more than one unit which enables to administer the THCV separately, simultaneously or sequentially to THC.

In an embodiment, the composition is a unit dosage form comprising less than or equal to 120 mg of THCV. In an embodiment, the composition comprises tetrahydrocannabinol (THC) and is a unit daily dosage form comprising less than or equal to 150 mg of THC.

According to the invention, it is preferred that the pharmaceutical composition is a unit dosage form comprising less than or equal to 150 mg of the THCV and higher than 1 mg of the THC.

It is furthermore preferred that the pharmaceutical composition is a unit dosage form comprising less than or equal to 150 mg of THCV in an oil formulation and higher than 1 mg of THC. Most preferable 150 mg THCV and less than 150 mg THC in oil formulations. For *Cannabis* simplex (medical grade) the preferred concentration range will be between 10-25% THCV and 10-25% of THC per gram of medication, wherein THCV is most preferably equal to or more than THC in absolute amounts.

A "unit dosage form" is to be understood as a maximum dose of medication that can be taken at any time or within a specified dosage period.

The unit dosage form preferably comprise a range of between about 1 and about 150 mg of each THCV and THC in oil preparations, wherein the amount of THC is preferably in the range of between about 1 and about 150 mg. More preferably, the amount of each THCV and THC in the unit dosage form is in the range of 20 to 100 mg respectively.

According to the invention, the composition further comprises Cannabigerol (CBG) or Cannabinodiol (CBND) or a mixture thereof, preferably in a ratio of THCV:CBG:CBND 10:1:5-1 10:1-5. Because CBG is a typical indica effect and actually an opposite effect of THC. Now it is known that THC induces hunger and THCV counteracts this, by combining the MEB with THCV, the antagonistic action against THC will become stronger from THCV and CBG, which causes the appetite to be suppressed more strongly. CBND is again a catalyst that ensures that the appetite-suppressing effects can be enhanced many times over. Preferably, the composition comprises a mixture of CBG and CBND, wherein the ratio of CBG:CBND by weight is between about 10:1 and about 1:10.

In an embodiment, the composition comprises tetrahydrocannabivarin (THCV), tetrahydrocannabinol (THC), Cannabigerol (CBG) and Cannabinodiol (CBND) in a ratio by weight of THCV:THC of between about 1:5 and about 5:1 and CBG:CBND of between about 10:1 and about 1:10.

In an embodiment of the pharmaceutical composition, the composition comprises less than 0.10 wt. % of cannabichromene (CBC) and/or cannabinol (CBN) based on the weight of THCV. In a preferred embodiment, the composition is substantially free of CBC or substantially free of CBN or substantially free of both CBC and CBN. In an embodiment, the ratio is THCV:CBC:CBN is 10:1:1-5, 1:10: 5-1 and 1:10:5-1 10:1-5.

The pharmaceutical composition according to the present invention is preferably packaged for delivery in a titratable dosage form. The term "titratable" is to be understood as meaning that the patient is provided with a medication that is in such a form that smaller dosages than the unit dose can be taken. Titration of dosages in a patient related manner, are beneficial to the patient as they are able to take smaller dosages of the medication until the drug is efficacious. As will be apparent to those skilled in the art, not all patients will require exactly the same dose of medication, for example patients of a larger build or patients having a faster metabolism. Different patients may also present with different degrees of complaints and as such may require larger or smaller doses in order to treat the complaint effectively. The benefits of such a dosage form over dosage forms such as tablets, where smaller doses are difficult to take, are therefore evident.

In an embodiment, the composition is a gel, a gel spray, a tablet, a liquid, a capsule, in a form suitable for vaporization or in a form suitable for nebulization.

Preferably, the pharmaceutical composition according to the invention is packaged for delivery such that delivery is targeted to an area selected from one or more of the following: sublingual, buccal, oral, rectal, nasal and the pulmonary system as vapor, intravenously, intra-arterially, topically, by injection, intraperitoneally, intrapleurally, orally, subcutaneously, intramuscularly, intraepidermally, or rectally. Illustrative methods of administration are vapor, orally and intraveneneously (IV). The oral formulations may be solutions, suspensions, suppositories, tablets, granules, powders, capsules, ointments, or creams. The IV formulation may be solutions or suspensions, including compositions comprising liposomes.

In the preparation of the pharmaceutical compositions according to the present invention, a solvent (e.g. water or physiological saline), a solubilising agent (e.g., ethanol, Polysorbates or Cremophor EL7), tonicity agents, preservatives, antioxidants, excipients (e.g. lactose, starch, crystalline cellulose, mannitol, maltose, calcium hydrogen phosphate, light silicic acid anhydride or calcium carbonate), binders (e.g. starch, polyvinylpyrrolidone, hydroxypropyl cellulose, ethyl cellulose, carboxy methyl cellulose or gum Arabic), lubricants (e.g. magnesium stearate, talc or hardened oils), and stabilisers (e.g. lactose, mannitol, maltose, polysorbates, macrogols, or polyoxyethylene hardened castor oils) can be added. If necessary, glycerin, dimethylacetarnide, 70% sodium lactate, a surfactant or a basic substance such as sodium hydroxide, ethylenediamine, ethanolamine, sodium bicarbonate, arginine, meglumine or trisaminoethane is added. Pharmaceutical preparations such as solutions, tablets granules or capsules can be formed with these components.

Additionally the pharmaceutical composition according to the present invention further comprises one or more carrier solvents. Preferably the carrier solvents are ethanol and/or propylene glycol. Preferably the ratio of ethanol to propylene and glycol is between 4:1 and 1:4. More preferably still the ratio is substantially 1:1.

Generally, unit dosages forms of the pharmaceutical composition according to the present invention are administered in such a way that they provide a dosage of about 10 mg to about 200 mg, preferably about 15 mg to about 150 mg, more preferably about 20 mg to about 100 mg per day of the THCV. Hence, the daily dose may include two or more unit dosage forms.

As a consequence, the present invention also relates to a pharmaceutical composition for a daily dosage schedule of about 10 mg to about 200 mg, preferably about 15 mg to about 150 mg, more preferably about 20 mg to about 100 mg of the THCV, on a Δ9-tetrahydrocannabivarin active weight basis, wherein the pharmaceutical composition comprises one or more unit dosage forms.

The present invention also relates to a kit adapted for a daily dosage schedule of about 10 mg to about 200 mg, preferably about 15 mg to about 150 mg, more preferably about 20 mg to about 100 mg of the THCV, said kit comprising one or more unit dosage forms of a pharmaceutical composition according to the present invention.

The composition according to the invention preferably has more THCV than THC and a bit more THCV than CBG but preferably more THC than CBG:THCV:CBG:CBND:THC by weight is between 10:1:1-5, 1:10: 5-1.

In an embodiment, the ratio THCV:CBND is 10:1. In an embodiment, the ratio THCV:CBG: is 5:1. In an embodiment, the ratio THCV:CBND:CBG is 10:1:1-5 10:1-5.

FIG. 1 shows the profiles for the different chemotypes. It can be seen from FIG. 1 that for the present invention that type 10 and type 12 are of main interest because of the present or absent cannabinoids.

EXAMPLES

Method of Preparation of Pharmaceutical Composition

Step 1: Chopping to predominantly 2-3 mm.

Step 2: Decarboxylate at 100-150° C. to form neutral forms.

Step 3: Extraction with a specific volume of Ethanol or liquid carbon.

Step 4: Removal by film-rotavoparization or depressuration of $CO_2$ resp.

Step 5: Winterisation: Winterisation removes unwanted components from the crude extract. The first step is to dilute the crude extract in ethanol and store the mixture at the freezing point of ethanol (114.1° C.) for at least 24 hours. This prompts the removal of lipids and waxes from the extract.

Step 6: Removal of unwanted waxes by cold filtration. Filtration: To remove precipitates and other particulates from the extract, one can use vacuum filtration via a Buchner funnel or a plate press. The filter micron range should be 0.45 or less.

Step 7: Removal of ethanol from the filtrate by thin film evaporation under reduced pressure, closed loop distillation. Distillation: To produce a cannabinoid-rich distillate product, one can either short path distillation, fractional distillation or wiped film distillation.

Step 8: CPC: Separating and/or purifying cannabinoids, comprising at least one liquid-liquid partition chromatography step, or the use of a centrifugal distribution chromatograph for liquid-liquid partition chromatography to separate and/or purify cannabinoids using a solvent selected from cyclohexane, heptane, n-heptane, iso-heptane, octane, n-octane, iso-octane, which is kept stationary by centrifugal force and a second immiscible liquid phase can be pumped through as a mobile phase. More details can be found in WO2016135346A1. Fractionation of neutral cannabinoids by CPC using the two-phase system hexane/acetone/acetonitrile, 5:2:3 (v:v:v, solvent system 2). The CPC is operated in ascending mode, with the lower (acetonitrile-rich) phase used as stationary phase and the upper (hexane-rich) upper phase as mobile phase. Flow-rate set at 5 ml/min and rotation speed at 600 rpm. The volume of stationary phase at 65 ml. Dissolve the sample to a final volume of 5 ml of upper phase for injection. Fraction size are collected. Analyses of fractions by TLC and further analysis by HPLC. Resulting Fraction contains a high proportion (>90%, preferably >95%) of the desired compound. This method is described in Hazekamp et al., Preparative Isolation of Cannabinoids from *Cannabis sativa* by Centrifugal Partition Chromatography, Journal of Liquid Chromatography & Related Technologies 27(15):2421-2439-December 2004.

Step 9: One or more (desired) isolated cannabinoids are selected and combined to be present in the pharmaceutical composition. Preferably, no other cannabinoids than the selected one(s) are present in the composition; however, trace amounts may be present. Preferably, the selected cannabinoids in the pharmaceutical composition are present in the same respective weight ratios as in the *Cannabis* strain.

Type 3 (Indian) and Type 8 (haze type) of the chemotype chart are taken as starting material for extraction and purification. Then the purified required cannabinoids (THCV, CBG, and CBND) form at least 95 (wt.)% of the composition in an oil, capsule or any form.

Example 1

THCV:CBG:CBND:THC by weight is between 10:1:1-5, 1:10: 5-1 and 1:10:5-1 10:1-5. The effect will be a strong inhibitory action on appetite and at the same time an energizing and boosting feeling. It will increase the antagonistic effect of this formulation on the CB1 receptor.

CLAUSES

1. Pharmaceutical composition comprising a tetrahydrocannabivarin for the prevention and treatment of overweight.
2. Pharmaceutical composition according to clause 1, wherein the tetrahydrocannabivarin is selected from the group consisting of Δ9-tetrahydrocannabivarin, Δ8-tetrahydrocannabivarin, and mixtures thereof.
3. Pharmaceutical composition according to clause 1, wherein the composition further comprises THC.
4. Pharmaceutical composition according to clause 3, wherein the composition comprises a TCHV and THC, wherein the ratio of THCV:THC by weight is between about 10:1 and about 1:10.
5. Pharmaceutical composition according to clause 4, wherein the ratio of THCV:THC by weight is between about 1:5 and about 5:1.
6. Pharmaceutical composition according to clause 4, wherein the ratio of THCV:THC by weight is about 10:1 and about 1:10.
7. Pharmaceutical composition according to clause 4, wherein the ratio of THCV:THC by weight is between about 1:1 and about 10:1.
8. Pharmaceutical composition according to clause 3, wherein THCV is administered separately, simultaneously or sequentially to THC.
9. Pharmaceutical composition according to clause 1, wherein the composition further comprises CBG, CBND or a mixture thereof.
10. Pharmaceutical composition according to clause 5, wherein the composition comprises further comprises a mixture of CBG and CBND, wherein the ratio of CBG:CBND by weight is between about 10:1 and about 1:10.
11. Pharmaceutical composition according to clause 1, wherein the composition is a unit dosage form comprising less than or equal to 120 mg of THCV.
12. Pharmaceutical composition according to clause 1, wherein the composition is a unit daily dosage form comprising less than or equal to 150 mg of THC.
13. Pharmaceutical composition according to clause 1, wherein the composition is packaged for delivery in a titratable dosage form.
14. Pharmaceutical composition according to clause 1, wherein the composition is a gel, a gel spray, a tablet, a liquid, a capsule, in a form suitable for vaporization or in a form suitable for nebulisation.
15. Pharmaceutical composition according to clause 1, wherein the overweight is associated with obesitas.
16. Method for treating a mammal suffering from overweight or a related disorder, wherein a pharmaceutical composition according to clause 1 is administered to said mammal.

The invention claimed is:

1. A composition comprising a mixture for use in the prevention and/or treatment of overweight, wherein the mixture consists essentially of tetrahydrocannabivarin (THCV), tetrahydrocannabinol (THC), cannabigerol (CBG) and cannabinodiol (CBND) in a ratio by weight of THCV: THC of between 1:5 and 5:1 and CBG: CBND of between 10:1 and 1:10.

2. The composition according to claim 1, wherein the tetrahydrocannabivarin (THCV) is selected from the group consisting of Δ9-tetrahydrocannabivarin (THCV), Δ8-tetrahydrocannabivarin (Δ8-THCV), and one or more mixtures thereof.

3. The composition of claim 1, wherein the composition is a unit dosage form comprising less than or equal to 120 mg of THCV.

4. The composition of claim 1, wherein the composition is a unit daily dosage form comprising less than or equal to 150 mg of THC.

5. The composition of claim 1, wherein the composition is packaged for delivery in a titratable dosage form.

6. The composition of claim 1, wherein the composition is a gel, a gel spray, a tablet, a liquid, a capsule, in a form suitable for vaporization or in a form suitable for nebulization.

7. The composition of claim 1, wherein the overweight is obesity.

8. The composition of claim 1, wherein the composition comprises less than 0.10 wt. % of cannabichromene (CBC) and/or cannabinol (CBN) based on the weight of THCV.

9. A composition comprising a mixture for use in the prevention and/or treatment of overweight, wherein the mixture consists essentially of tetrahydrocannabivarin (THCV), tetrahydrocannabinol (THC), cannabigerol (CBG) and cannabinodiol (CBND) in a ratio by weight of THCV: THC of between 1:5 and 5:1 and CBG:CBND of between 10:1 and 1:10, wherein at least one of the THCV, the THC, the CBG, and the CBND is synthetic.

* * * * *